(12) United States Patent
Ohuchi et al.

(10) Patent No.: US 10,117,636 B2
(45) Date of Patent: Nov. 6, 2018

(54) ULTRASONIC DIAGNOSTIC APPARATUS, ULTRASONIC IMAGE PROCESSING APPARATUS, MEDICAL IMAGE DIAGNOSTIC APPARATUS, AND MEDICAL IMAGE PROCESSING APPARATUS

(75) Inventors: Hiroyuki Ohuchi, Otawara (JP); Shinichi Hashimoto, Otawara (JP); Yasuhiko Abe, Otawara (JP); Tetsuya Kawagishi, Nasushiobara (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 68 days.

(21) Appl. No.: 12/692,023

(22) Filed: Jan. 22, 2010

(65) Prior Publication Data

US 2010/0198071 A1 Aug. 5, 2010

(30) Foreign Application Priority Data

Jan. 30, 2009 (JP) ................................ 2009-019673
Dec. 2, 2009 (JP) ................................ 2009-274673

(51) Int. Cl.
*A61B 8/08* (2006.01)
*G06F 19/00* (2018.01)

(52) U.S. Cl.
CPC ................ *A61B 8/08* (2013.01); *G06F 19/00* (2013.01); *A61B 8/0883* (2013.01); *A61B 8/483* (2013.01); *A61B 8/5223* (2013.01)

(58) Field of Classification Search
CPC ......... A61B 8/08; A61B 8/0883; A61B 8/483; A61B 8/5223
USPC .......................... 600/437, 443, 438; 382/128
See application file for complete search history.

(56) References Cited

U.S. PATENT DOCUMENTS 7,050,610 B2 * 5/2006 Chen et al. .................... 382/128
2006/0079777 A1 * 4/2006 Karasawa ...................... 600/443
2008/0077032 A1 * 3/2008 Holmes .................. A61B 5/055
600/523

(Continued)

FOREIGN PATENT DOCUMENTS

JP 2003-250804 9/2003
JP 2004-267393 9/2004

(Continued)

OTHER PUBLICATIONS

Abe et al., "Two and Three Dimensional Wall Motion Analysis", Medical Review, Toshiba Medical Systems, May 19, 2008, pp. 1-4.*

(Continued)

*Primary Examiner* — Katherine Fernandez
(74) *Attorney, Agent, or Firm* — Oblon, McClelland, Maier & Neustadt, L.L.P.

(57) ABSTRACT

Position coordinate information of each point three-dimensionally forming a tissue corresponding to a diagnosis target at each time phase is obtained, a quantitative value for evaluating the movement of the tissue corresponding to the diagnosis target is calculated by using the position information, and the result is output in a predetermined form. Accordingly, since the quantitative value for evaluating the movement is calculated by using the three-dimensional position coordinate information without converting wall movement information obtained by a three-dimensional tracking process into two-dimensional information, it is possible to provide medical information with a higher degree of precision.

19 Claims, 4 Drawing Sheets

(56) References Cited

U.S. PATENT DOCUMENTS

2008/0317316 A1* 12/2008 Ohuchi et al. ............... 382/131
2009/0054438 A1* 2/2009 Ronai ................... C07C 235/82
                                                        514/237.5
2011/0103657 A1* 5/2011 Kang et al. ................. 382/128

FOREIGN PATENT DOCUMENTS

JP      2007-222533 A    9/2007
JP      2008-301920 A    12/2008

OTHER PUBLICATIONS

Herz et al., "Parameterization of Left Ventricular Wall Motion for Detection of Regional Ischemia", Annals of Biomedical Engineering, vol. 33, No. 7, Jul. 2005, pp. 912-919.*
Gopal et al., "Left Ventricular Volume and Endocardial Surface Area by Three-Dimensional Echocardiography: Comparison with Two-Dimensional Echocardiography and Nuclear Magnetic Resonance Imaging in Normal Subjects", J Am Coll Cardiol, vol. 22, No. 1, Jul. 1993, pp. 258-270.*
Kobayashi et al., "Abstract 243: Area Strain by 3D Wall Motion Tracking Method is Useful to Detect Adenosine-Induced Myocardial Dysfunction: Comparisons with 99mTc Myocardial Perfusion Sciintigraphy", Circulation, vol. 120, Issue Suppl. 18, Nov. 3, 2009.*
Office Action dated Oct. 29, 2013 in Japanese Patent Application No. 2009-274673 (with English language translation).
Office Action dated Mar. 24, 2015, in Japanese Patent Application No. 2014-114416.

* cited by examiner

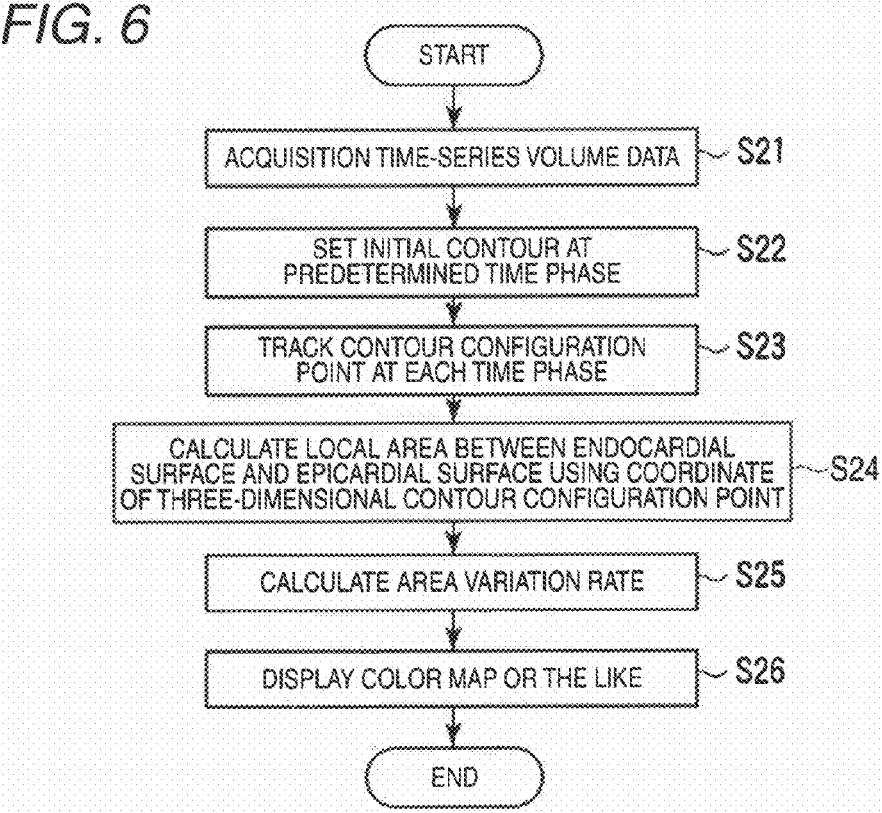
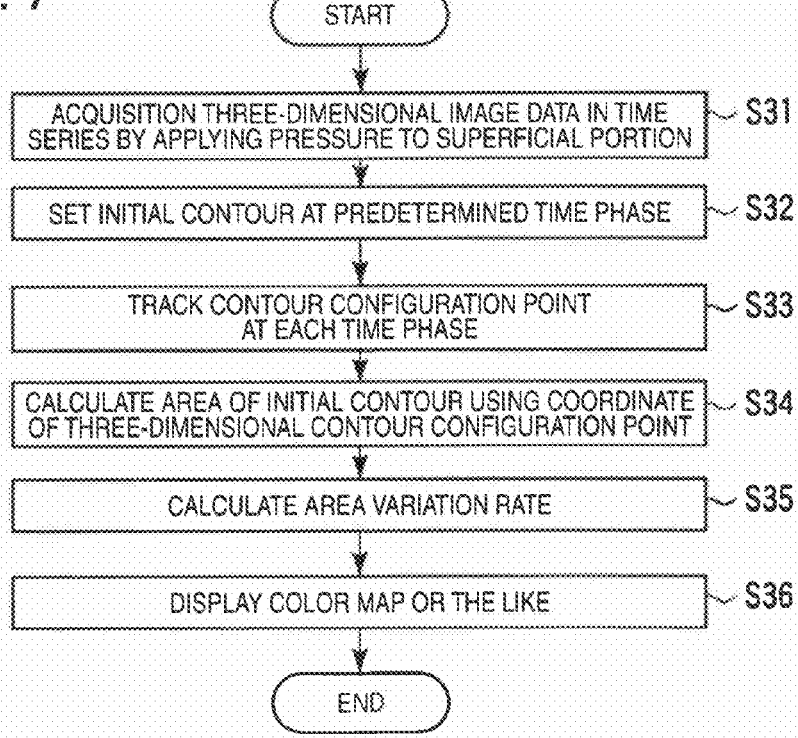

ULTRASONIC DIAGNOSTIC APPARATUS, ULTRASONIC IMAGE PROCESSING APPARATUS, MEDICAL IMAGE DIAGNOSTIC APPARATUS, AND MEDICAL IMAGE PROCESSING APPARATUS

CROSS-REFERENCE TO RELATED APPLICATIONS

This application is based upon and claims the benefit of priority from prior Japanese Patent Applications No. 2009-019673, filed Jan. 30, 2009; and No. 2009-274673, filed Dec. 2, 2009, the entire contents of both of which are incorporated herein by reference.

BACKGROUND OF THE INVENTION

1. Field of the Invention

The present invention relates to an ultrasonic diagnostic apparatus capable of obtaining tissue movement information such as cardiac wall movement information, an ultrasonic image processing apparatus performing an imaging process by using the tissue movement information obtained by the ultrasonic diagnostic apparatus, a medical image diagnostic apparatus, and a medical image processing apparatus.

2. Description of the Related Art

In an ultrasonic diagnosis, a heartbeat or a fetus's movement state may be obtained in real time just by touching a body surface with an ultrasonic probe and the ultrasonic diagnosis may be repeated due to the reliability thereof. In addition, since the size of the system of the ultrasonic diagnostic apparatus is smaller than those of other diagnostic apparatuses such as an X-ray diagnostic apparatus, a CT diagnostic apparatus, and an MRI diagnostic apparatus, the ultrasonic diagnosis may be easily performed by disposing the ultrasonic diagnostic apparatus at a position on the side of the bed. For this reason, the ultrasonic diagnosis is a simple diagnosis method. The size of the ultrasonic diagnostic apparatus used in the ultrasonic diagnosis is different depending on the types of the functions thereof, and a small-sized ultrasonic diagnostic apparatus which is able to be carried by one hand is developed. Unlike the X-ray diagnosis, the ultrasonic diagnosis has no influence of a radiation exposure, and hence the ultrasonic diagnosis may be used for the obstetrics and gynecology or the home medical treatment, and the like.

Generally, in the diagnosis of the body tissue, it is very important to objectively and quantitatively evaluate the function of the body tissue such as a myocardium of a heart. Recently, a quantitative evaluation method has been proposed which obtains image data of a heart using the above-described ultrasonic diagnostic apparatus and performs a quantitative evaluation based on the image data. For example, in Jpn. Pat. Appln. KOKAI Publication No. 2003-250804, a method is proposed which obtains movement information such as displacement or strain of a tissue by tracking a speckle pattern of an image. This method is to perform a pattern matching process using the speckle pattern of the image, and is called a Speckle Tracking Process. Recently, a three-dimensional tracking process for three-dimensional volume data is able to be performed in addition to a tracking process for a two-dimensional tomographic image. As a detailed example, when a myocardium of a heart is evaluated, volume data for each cardiac time phase is obtained by transmitting an ultrasonic wave to the heart by using a three-dimensional ultrasonic diagnostic apparatus. In addition, when a pattern matching process using a three-dimensional speckle tracking process is performed, it is possible to obtain displacement of an endocardium and an epicardium for each cardiac time phase. Then, on the basis of the displacement of the endocardium and the epicardium at each time phase, it is possible to obtain strain or velocity of the myocardium at each time phase. By obtaining the wall movement information, the wall movement of the myocardium is evaluated.

However, the wall movement parameter such as strain or velocity obtained in the known three-dimensional tracking process is a two-dimensional parameter, and the three-dimensional wall movement information obtained by the three-dimensional tracking process is converted into two-dimensional information. For this reason, the three-dimensional wall movement information calculated by the three-dimensional tracking process is not sufficiently provided to a user.

BRIEF SUMMARY OF THE INVENTION

An object of the invention is to provide an ultrasonic diagnostic apparatus capable of performing a three-dimensional and quantitative wall movement evaluation with a high degree of precision by using wall movement information obtained by calculating a local volume between an endocardium and an epicardium or a local area of the endocardium or the epicardium on the basis of tissue position information such as three-dimensional endocardium and epicardium position information calculated through a three-dimensional tracking process, an ultrasonic image processing apparatus, a medical image diagnostic apparatus, and a medical image processing apparatus.

According to an aspect of the present invention, there is provided that an ultrasonic diagnostic apparatus includes: a data obtaining unit which obtains time-series volume data by scanning a three-dimensional region, including a predetermined portion of a patient, through an ultrasonic wave; a tracking unit which receives a setting of an outline of a tissue for volume data at a predetermined time phase among the time-series volume data, and tracks a position of each point forming the outline of volume data at the other time phases through a pattern matching process; and a calculation unit which calculates a quantitative value for each time phase using at least one of a local area and a local volume of the outline on the basis of the position of each point forming the outline obtained by the tracking process.

According to another aspect of the present invention, there is provided that an ultrasonic image processing apparatus includes: a storage unit which stores time-series volume data obtained by scanning a three-dimensional region, including a predetermined portion of a patient, through an ultrasonic wave; a tracking unit which receives a setting of an outline of a tissue for volume data at a predetermined time phase among the time-series volume data, and tracks a position of each point forming the outline of volume data at the other time phases through a pattern matching process; and a calculation unit which calculates a quantitative value for each time phase using at least one of a local area and a local volume of the outline on the basis of the position of each point forming the outline obtained by the tracking process.

According to yet another aspect of the present invention, there is provided that a medical image diagnostic apparatus includes: a data obtaining unit which obtains time-series volume data for a three-dimensional region including a predetermined portion of a patient; a tracking unit which receives a setting of an outline of a tissue for volume data at a predetermined time phase among the time-series volume data, and tracks a position of each point forming the outline of volume data at the other time phases through a pattern matching process; and a calculation unit which calculates a quantitative value for each time phase using at least one of a local area and a local volume of the outline on the basis of the position of each point forming the outline obtained by the tracking process.

According to yet another aspect of the present invention, there is provided that a medical image processing apparatus includes: a storage unit which stores time-series volume data for a three-dimensional region including a predetermined portion of a patient; a tracking unit which receives a setting of an outline of a tissue for volume data at a predetermined time phase among the time-series volume data, and tracks a position of each point forming the outline of volume data at the other time phases through a pattern matching process; and a calculation unit which calculates a quantitative value for each time phase using at least one of a local area and a local volume of the outline on the basis of the position of each point forming the outline obtained by the tracking process.

BRIEF DESCRIPTION OF THE SEVERAL VIEWS OF THE DRAWING

FIG. 6 is a flowchart showing a sequence of the three-dimensional movement information calculation process according to a third embodiment.

FIG. 7 is a flowchart showing a sequence of the three-dimensional movement information calculation process according to a fourth embodiment.

DETAILED DESCRIPTION OF THE INVENTION

Figure 1:
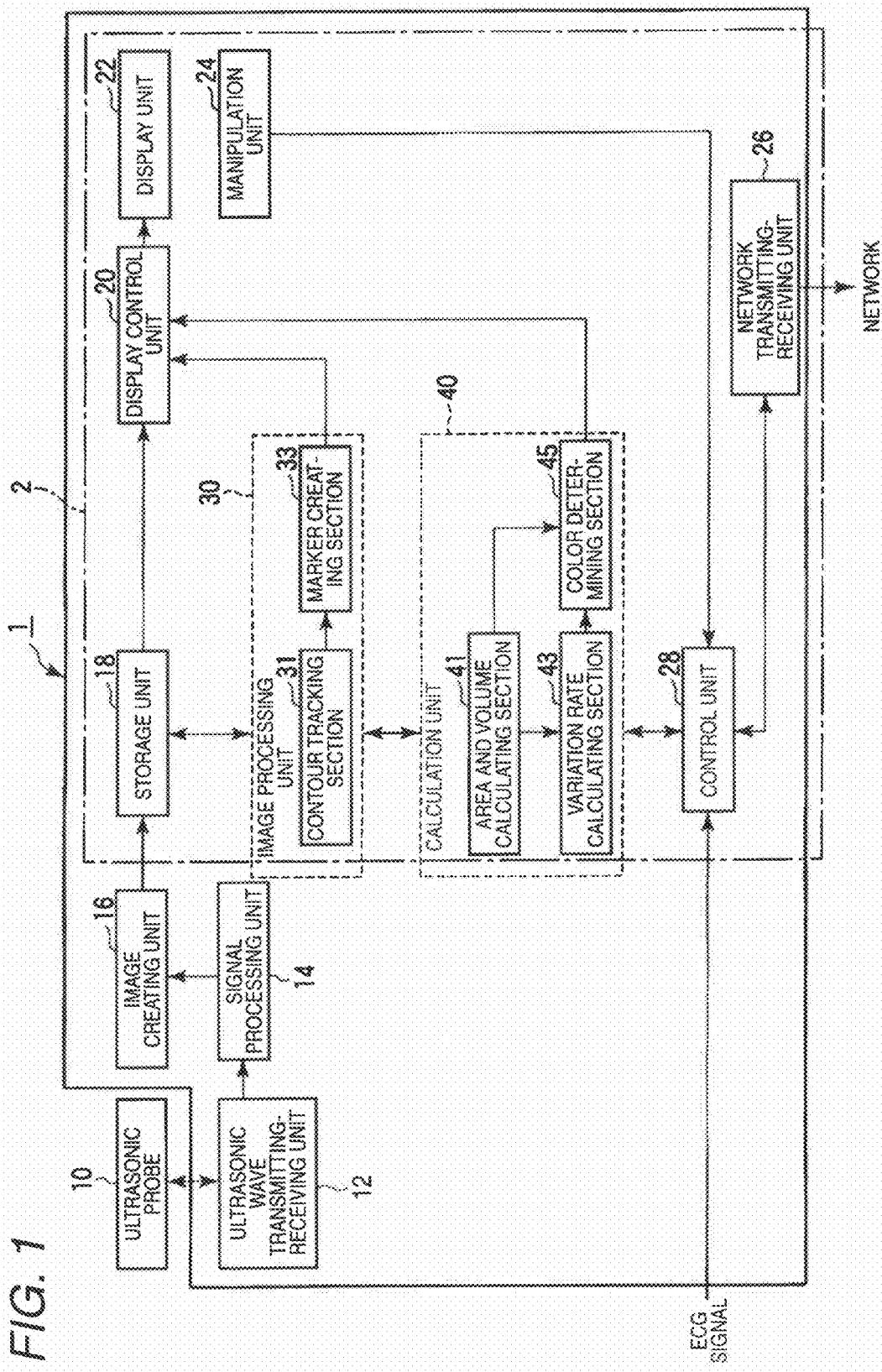
FIG. 1 is a block diagram showing a configuration of an ultrasonic diagnostic apparatus according to a first embodiment.

Hereinafter, first to fourth embodiments of the invention will be described with reference to the accompanying drawings. Additionally, in the following description, the same reference numerals will be given to the constituents substantially having the same function and configuration, and the repetitive description thereof will be made if necessary.

First Embodiment

FIG. 1 is a block diagram showing a configuration of an ultrasonic diagnostic apparatus according to the first embodiment. As shown in FIG. 1, an ultrasonic diagnostic apparatus 1 includes an ultrasonic probe 10, an ultrasonic wave transmitting-receiving unit 12, a signal processing unit 14, an image creating unit 16, a storage unit 18, a display control unit 20, a display unit 22, a manipulation unit 24, a network transmitting-receiving unit 26, a control unit 28, an image processing unit 30, and a calculation unit 40. Hereinafter, the function of each of constituents will be described.

The ultrasonic probe 10 generates ultrasonic waves on the basis of a driving signal output from the ultrasonic wave transmitting-receiving unit 12, and includes plural ultrasonic vibrators (piezoelectric vibrators) which convert waves reflected from a patient into electric signals, a matching layer which is provided in the piezoelectric vibrators, a packing member which prevents the ultrasonic waves from being transmitted backward from the piezoelectric vibrators, and the like. When the ultrasonic waves are transmitted from the ultrasonic probe 10 to a patient P, the transmitted ultrasonic waves are sequentially reflected by discontinuous surfaces of acoustic impedance of a body tissue, and are transmitted as echo signals to the ultrasonic probe 10. The amplitudes of the echo signals are dependent on the acoustic impedance difference of the discontinuous surfaces used to reflect the ultrasonic waves. In addition, when the transmitted ultrasonic pulses are reflected by a surface of a moving blood stream, a cardiac wall, or the like, the echo signals are influenced by a frequency shift depending on a velocity component of a moving object in an ultrasonic wave transmitting direction due to a Doppler effect.

In addition, in the first, second, and third embodiments, for the detailed description, the ultrasonic probe 10 is referred to as a two-dimensional array probe in which the ultrasonic vibrators are arranged in a two-dimensional matrix shape. However, the invention is not limited to this example, but as the ultrasonic probe 10, for example, a one-dimensional array probe may be used which is able to perform a swinging scanning operation through a manual or mechanical operation.

The ultrasonic wave transmitting unit 12 includes a trigger generating circuit, a delay circuit, a pulser circuit, and the like which are not shown in the drawings. The pulser circuit repeatedly generates rate pulses at a predetermined rate frequency fr Hz (period; 1/fr second) so as to form the transmitted ultrasonic waves. The delay circuit converges the ultrasonic waves for each channel into a beam shape and gives a delay time required for determining the transmitting directivity to each rate pulse. The trigger generating circuit applies a driving pulse to the probe 12 at a timing based on the rate pulse.

Further, the ultrasonic wave transmitting-receiving unit 12 includes an amplifier circuit, an A/D converter, an adder, and the like which are not shown in the drawings. The amplifier circuit amplifies the echo signals obtained via the probe 10 for each channel. The A/D converter gives a delay time required for determining the receiving directivity to the amplified echo signals, and the amplified echo signals are subjected to an adding process by the adder. By means of the adding process, a reflection component in the direction according to the receiving directivity of the echo signals is emphasized, and an ultrasonic wave transmitting-receiving synthetic beam is formed by the receiving directivity and the transmitting directivity.

The signal processing unit 14 receives the echo signals from the ultrasonic wave transmitting-receiving unit 12, and performs a log amplifying process, an envelope detecting process, and the like so as to create data in which the signal strength is represented by a luminance. The data is transmitted to the image creating unit 16, and is displayed as a B-mode image on the display unit 22, where in the B-mode image, the strength of the reflected wave is represented by a luminance. In addition, the signal processing unit 14 performs a frequency analysis of the velocity information from the echo signals transmitted from the ultrasonic wave transmitting-receiving unit 12, extracts an echo component of a blood stream, a tissue, or a visualizing agent using the Doppler effect, and then obtains blood stream information such as an average velocity, a distribution, and a power for plural points.

Generally, the image creating unit 16 creates the ultrasonic diagnostic image as the display image by converting (scan-converting) a scanning line signal row of an ultrasonic scanning into a scanning line signal row of a general video format represented by a television or the like.

The storage unit 18 stores, for example, a freeze image and ultrasonic images corresponding to plural frames obtained before the freeze image. When the images stored in the storage unit 18 are displayed as a cine display, an ultrasonic video is able to be displayed. The storage unit 18 stores freeze images, images instructed to be stored, images obtained in the past, and the like. In addition, the storage unit 18 stores a predetermined scan sequence, an exclusive program for realizing a three-dimensional movement information calculation function to be described later, a control program for performing an image creating process and an image displaying process, a program for creating diagnostic information (a patient ID, a doctor's opinion, and the like), a diagnostic protocol, a transmitting-receiving condition, and a body mark, and other data groups.

The display unit 22 displays morphological information (B-mode image) inside the body, blood stream information (an average velocity image, a distribution image, a power image, and the like), and the combination thereof as an image thereon on the basis of a video signal output from a scan converter 25.

The manipulation unit 24 is connected to an apparatus body 11, and includes various switches, buttons, a track ball, a mouse, a keyboard, and the like which are used to allow an operator to input various instructions, conditions, ROI (region of interest) setting instructions, various image quality condition setting instructions, input instructions for the number of synthetic beams or the number of used beams to be described later, and the like to the ultrasonic diagnostic apparatus 1. For example, when the operator manipulates an end button or a FREEZE button of the manipulation unit 24, the ultrasonic wave transmitting-receiving operation ends, and the ultrasonic diagnostic apparatus becomes a pause state.

The control unit 28 functions as an information processing device (calculator), and controls the operation of the ultrasonic diagnostic apparatus 1. The control unit 28 reads out an exclusive program for realizing the three-dimensional movement information calculation function to be described later and a control program for performing a predetermined image creating-displaying process or the like from the storage unit 18, and loads the programs on its memory so as to perform a calculation and control or the like for various processes.

The network transmitting-receiving unit 26 is an interface used for the connection to a network. The data such as an ultrasonic image or the analysis result obtained by the apparatus is able to be transmitted to other devices via the network by the network transmitting-receiving unit 26.

The image processing unit 30 includes an outline tracking section 31 and a marker creating section 33. The outline tracking section 31 performs a pattern matching process between volume data at different time phases so as to track each point three-dimensionally forming a tissue corresponding to a diagnosis target such as a cardiac wall outline for each volume data at each time phase. The marker creating section 33 sets a marker at a desired position or region of the volume data at each time phase on the basis of the instruction through the manipulation unit 23 or the like.

The calculation unit 40 includes an area and volume calculating section 41, a variation rate calculating section 43, and a color determining section 45. The area and volume calculating section 41 calculates a quantitative value such as an area and a volume for evaluating a movement of the tissue on the basis of position coordinate information of each point three-dimensionally forming the tissue to be tracked at each time phase. The variation rate calculating section 43 calculates a variation rate of an area or a volume from a reference time phase (for example, an initial time phase) to a desired time phase. The color determining section 45 determines a color corresponding to a degree of a variation rate of an area or the like for each position.

Three-dimensional Movement Information Calculation Function

Next, the three-dimensional movement information calculation function included in the ultrasonic diagnostic apparatus 1 will be described. This function is used to obtain position coordinate information of each point three-dimensionally forming the tissue corresponding to the diagnosis target at each time phase, calculates the quantitative value for evaluating the movement of the tissue corresponding to the diagnosis target by using the position information, and outputs the result in a predetermined form. In addition, in the first, second, and third embodiments, for the detailed description, a case will be described in which a heart is the diagnosis target. However, the invention is not limited to this example, but any internal organ or portion may be set to the diagnosis target if the tissue thereof requires the movement evaluation.

Figure 2:
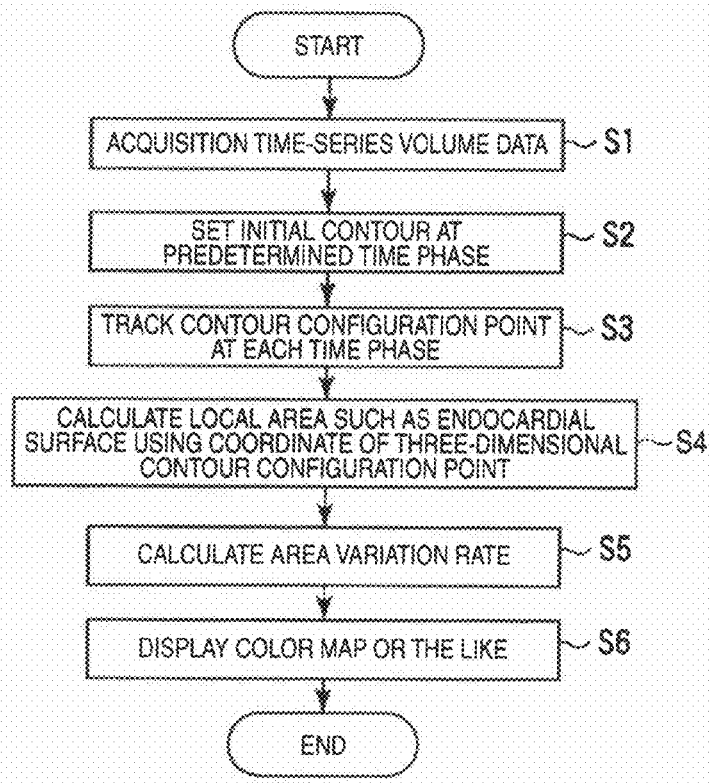
FIG. 2 is a flowchart showing a sequence of a process (three-dimensional movement information calculation process) in accordance with a three-dimensional movement information calculation function according to the first embodiment.

FIG. 2 is a flowchart showing a sequence of a process (three-dimensional movement information calculation process) in accordance with the three-dimensional movement information calculation function. By referring to FIG. 2, the contents of the three-dimensional movement information calculation process will be described.

First, volume data (hereinafter, referred to as the "time-series volume data group") throughout a period equal to or more than at least one heartbeat is collected from an entire heart or a desired observation portion of a heart of a certain patient (Step S1). That is, volume data of a time series (at least one heartbeat) based on a certain time is collected from the desired observation portion of the heart of the certain patient through a cardiac apex approach by using a two-dimensional array probe.

Next, the control unit 28 set an initial outline for volume data at a predetermined time phase on the basis of the instruction through the manipulation unit 24 (Step S2). That is, a desired time phase is designated through the manipulation unit 24. In response to the designation, the control unit 28 applies an MPR (Multi Planer Reconstruction) process to the volume data of the time phase so as to create an MPR image (image data of an arbitrary section), and displays the result on the display unit 22. On the displayed MPR image, a papillary muscle or a chorda tendinea is displayed in addition to an endocardium and an epicardium. The operator designates the outline of the endocardium through the manipulation unit 24 while observing the displayed MPR image so that the papillary muscle or the chorda tendinea displayed on the volume data of the heart is not included.

When such a designation is performed on other plural MPR images of the time phase, the three-dimensional outline of the endocardium is set on the volume data. In addition, in the epicardium, in the same manner, when the outline of the epicardium is designated on the plural MPR images of the time phase through the manipulation unit 24, the three-dimensional outline of the epicardium is set.

Figure 3:
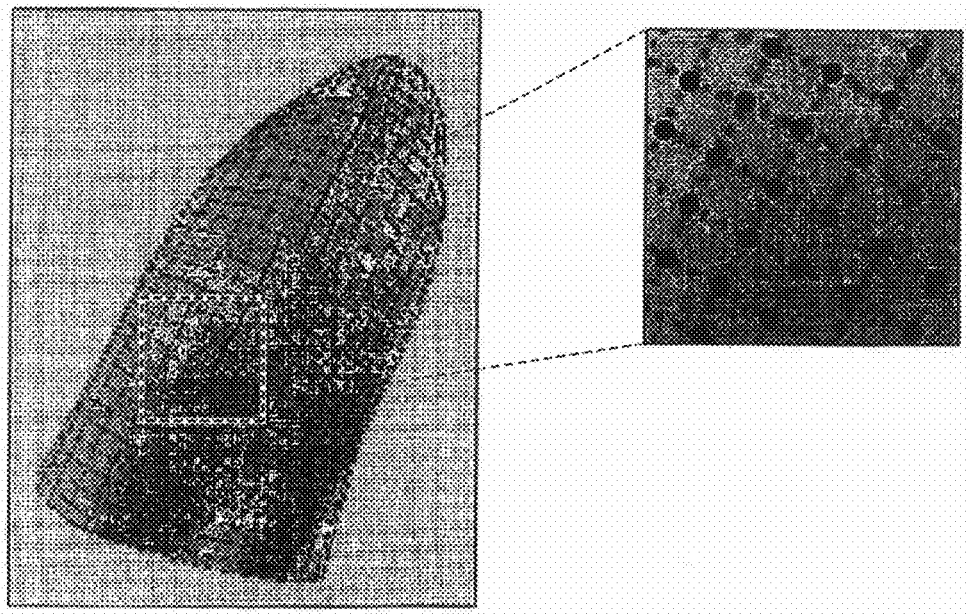
FIG. 3 is a diagram showing an example of a position of each point (configuration point) forming three-dimensional outlines of an endocardium and an epicardium designated by an initial outline.

When the three-dimensional outlines of the predetermined time phase are designated by the operator, the outline tracking section 31 performs a pattern matching process between two volume data by using a speckle pattern so as to obtain the position of each point (configuration point) forming the three-dimensional outlines of the endocardium and the epicardium designated by the initial outline for each volume data obtained at each cardiac time phase as shown in FIG. 3. In addition, the outline tracking section 31 tracks the configuration points of the three-dimensional outlines of the endocardium and the epicardium in time, and obtains the coordinate information of the configuration points of the three-dimensional outlines of the endocardium and the epicardium at each time phase (Step S3).

Figure 4:
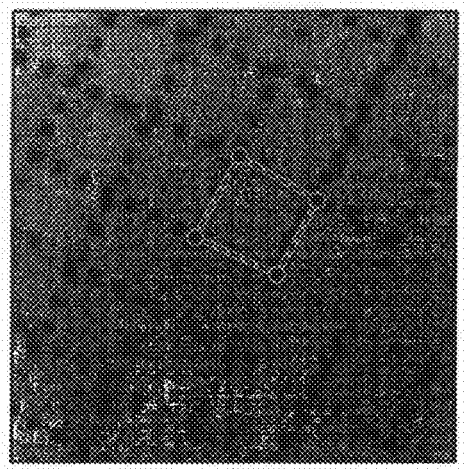
FIG. 4 is a diagram illustrating a calculation of a local area of an endocardial surface using coordinate information of each point forming the three-dimensional outline.

Next, the area and volume calculating section 41 obtains, for example, a local area of a endocardial surface on the basis of the coordinate information of each point forming the three-dimensional outlines of the endocardium and the epicardium at each cardiac time phase (Step S4). The area is calculated on the basis of the coordinate information of each point forming the three-dimensional outlines as shown in FIG. 4. For example, the local area of the endocardium may be calculated by using the Heron's formula for calculating the area of the triangle on the basis of the length of three sides. The Heron's formula is to calculate an area S by the following expression (1) when the length of the hypotenuse is set to a, b, and c. In addition, a, b, and c may be calculated on the basis of the coordinate information of each point forming the three-dimensional outlines.

[Expression 1]

$$S = \{s(s-a)(s-b)(s-c)\}^{1/2} \quad (1)$$

Here, $s = (a+b+c)/2$

Next, the variation rate calculating section 43 calculates the variation rate on the basis of the area at the initial time phase on the basis of the calculated area (Step S5). In addition, when the area at the time phase t is set to S(t), the area variation rate may be obtained by calculating the value of $\{S(t)-S(0)\}/S(0)$.

Next, the color determining section 45 determines a color corresponding to the degree of the area variation rate. The display control unit 20 displays the area variation rate on the display unit 22 in a color display mode so as to be overlapped with a volume image, an MPR image, a Polar-Map image, and the like by using coordinate information of each position at each cardiac time phase and information displaying a color allocated to the position (Step S6). In the color display mode, for example, the sign "+" of the area variation rate is displayed as a cold color (for example, blue), the sign "−" thereof is displayed as a warm color (for example, red), and the degree of the variation rate is displayed as a luminance (or color). In the normal myocardium in which the pump function of the heart is sufficiently maintained, since the area of the endocardial surface decreases during the systole, the warm color is displayed. In addition, the luminance thereof gradually increases until the end of systole, and the luminance thereof abruptly decreases at the beginning of the diastole. Meanwhile, when a portion having a reduced systole ability occurs due to the occurrence of the myocardial ischemia, the area variation rate deteriorates in the region. For this reason, a degree of an increase in luminance during the systole is smaller than that of the normal myocardium, and the luminance of the warm color decreases at the end of systole. In a portion having a reduced diastole ability, the decrease rate of the luminance at the beginning of the diastole becomes small compared with the normal myocardium. Accordingly, it is possible to easily distinguish the portions having abnormal systole ability and diastole ability from the normal myocardium through a three-dimensional quantitative method.

Effect

According to the ultrasonic diagnostic apparatus, the position coordinate information of each point three-dimensionally forming the tissue corresponding to the diagnosis target at each time phase is obtained, the quantitative value for evaluating the movement of the tissue corresponding to the diagnosis target is calculated by using the position information, and then the result is output in a predetermined form. Accordingly, since the quantitative value for evaluating the movement is calculated by using the three-dimensional position coordinate information without converting the wall movement information obtained by the three-dimensional tracking process into the two-dimensional information, it is possible to provide medical information with a higher degree of precision.

Second Embodiment

Next, a second embodiment of the invention will be described. In the ultrasonic diagnostic apparatus 1 according to the second embodiment, a local volume between the endocardium and the epicardium is obtained on the basis of the coordinate information of each point forming the three-dimensional outlines of the endocardium and the epicardium at each time phase.

Figure 5:
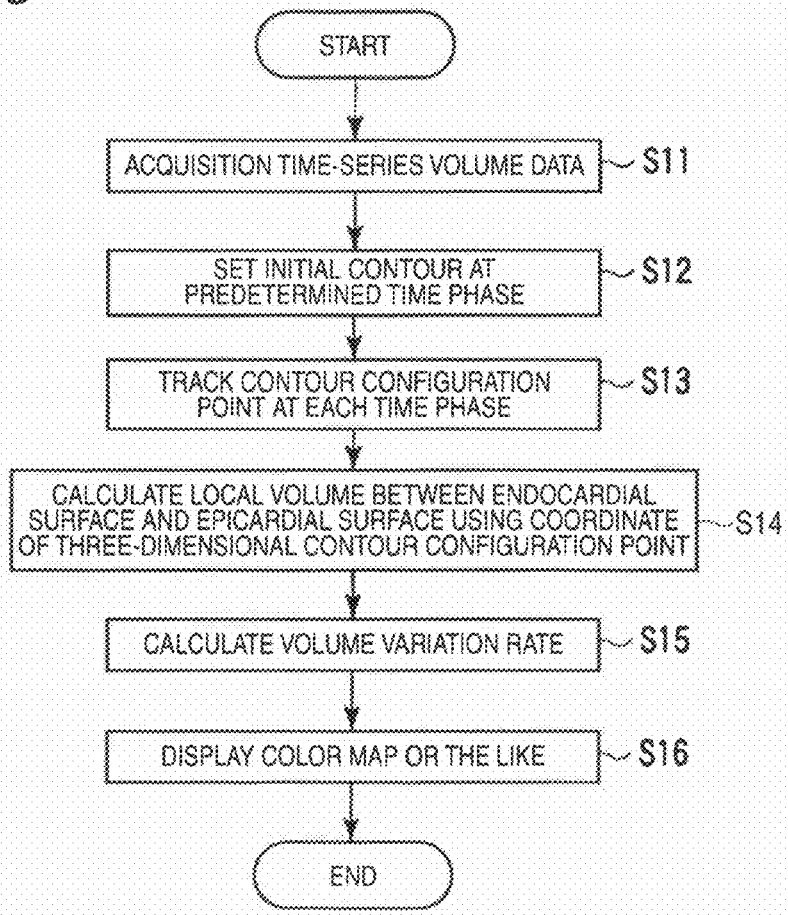
FIG. 5 is a flowchart showing a sequence of the three-dimensional movement information calculation process according to a second embodiment.

FIG. 5 is a flowchart showing a sequence of the three-dimensional movement information calculation process according to the second embodiment. Compared with the process (process shown in FIG. 2) of the first embodiment, the contents of Step S14 and Step S15 are different. Hereinafter, the contents of Step S14 and Step S15 will be described.

The area and volume calculating section 41 obtains, for example, a volume between the endocardium and the epicardium on the basis of the coordinate information of each point forming the three-dimensional outlines of the endocardium and the epicardium at each time phase (Step S14). As in the first embodiment, the volume is calculated on the basis of the coordinate information of each point forming the three-dimensional outline. For example, the following expression capable of calculating the volume of the tetrahedron may be used. When the coordinates of four apexes O, A, B, and C of the tetrahedron are respectively set to O (0, 0, 0), A $(x_1, y_1, z_1)$, B $(x_2, y_2, z_2)$, and C $(x_3, y_3, z_3)$, the volume V of the tetrahedron OABC is obtained by the following expression (2).

[Expression 2]

$$V = \text{absolute value of } \frac{1}{6} \begin{vmatrix} x_1 & y_1 & z_1 & 1 \\ x_2 & y_2 & z_2 & 1 \\ x_3 & y_3 & z_3 & 1 \\ 0 & 0 & 0 & 1 \end{vmatrix} \quad (2)$$

Since each of the points O, A, B, and C is coordinate information of each point forming the three-dimensional outline, the volume is obtained by the above-described expression (2). In addition, after the length of each side is obtained, the volume may be calculated by using the Heron's formula of space.

Next, the variation rate calculating section 43 calculates the variation rate from the volume at the initial time phase on the basis of the calculated volume (Step S15). In addition, when the volume at the time phase t is set to V(t), the volume variation rate may be obtained by calculating the value of $\{V(t)-V(0)\}/V(0)$).

Next, the color determining section 45 determines a color corresponding to the degree of the volume variation rate. The display control unit 20 displays the volume variation rate on the display unit 22 in a color display mode so as to be overlapped with a volume image, an MPR image, a Polar-Map image, and the like by using coordinate information of each position at each cardiac time phase and information displaying a color allocated to the position (Step S16).

According to the above-described configuration, the position coordinate information of each point three-dimensionally forming the tissue corresponding to the diagnosis target at each time phase is obtained, the local volume between the endocardium and the epicardium is obtained as the movement information of the moving organ by using the position information, and then the variation rate is calculated on the basis of the result. Accordingly, as in the first embodiment, since the quantitative value for evaluating the movement is calculated by using the three-dimensional position coordinate information without converting the wall movement information obtained by the three-dimensional tracking process into the two-dimensional information, it is possible to provide medical information with a higher degree of precision.

Third Embodiment

Next, a third embodiment of the invention will be described. In the ultrasonic diagnostic apparatus 1 according to the third embodiment, a local area between the endocardium and the epicardium is obtained on the basis of the coordinate information of each point forming the three-dimensional outlines of the endocardium and the epicardium at each time phase.

FIG. 6 is a flowchart showing a sequence of the three-dimensional movement information calculation process according to the third embodiment of the invention. Compared with the case of the process (process shown in FIG. 2) of the first embodiment, the contents in Step S24 and Step S25 are different. Hereinafter, the contents in Step S24 and Step S25 will be described.

The area and volume calculating section 41 obtains a local area between the endocardium and the epicardium on the basis of the coordinate information of each point forming the three-dimensional outlines of the endocardium and the epicardium at each time phase (Step S24). As in the first embodiment, for example, the local area between the endocardium and the epicardium is calculated by using the Heron's formula for calculating the area of the triangle on the basis of the length of three sides.

Next, the variation rate calculating section 43 calculates the variation rate on the basis of the area at the initial time phase on the basis of the calculated area (Step S25). In addition, as in the first embodiment, when the area at the time phase t is set to S(t), the area variation rate may be obtained by calculating the value of $\{S(t)-S(0)\}/S(0)$.

Next, the color determining section 45 determines a color corresponding to the degree of the local area variation rate between the endocardium and the epicardium. The display control unit 20 displays the local area variation rate on the display unit 22 in a color display mode so as to be overlapped with a volume image, an MPR image, a Polar-Map image, and the like by using coordinate information of each position at each cardiac time phase and information displaying a color allocated to the position (Step S26).

According to the above-described configuration, the position coordinate information of each point three-dimensionally forming the tissue corresponding to the diagnosis target at each time phase is obtained, the local area between the endocardium and the epicardium is obtained as the movement information of the moving organ by using the position information, and then the variation rate is calculated on the basis of the result. Accordingly, as in the first and second embodiments, since the quantitative value for evaluating the movement is calculated by using the three-dimensional position coordinate information without converting the wall movement information obtained by the three-dimensional tracking process into the two-dimensional information, it is possible to provide medical information with a higher degree of precision.

Fourth Embodiment

Next, a fourth embodiment of the invention will be described. In the ultrasonic diagnostic apparatus 1 according to the fourth embodiment, when a superficial portion of the patient is set to the diagnosis target, and a resiliency diagnosis (elastography) for evaluating the elasticity (hardness) of the local area is performed on the basis of a variation generated when the superficial portion is pressed or not pressed by the two-dimensional array probe, the three-dimensional movement information calculation process according to the first, second, and third embodiments are applied. In addition, in the fourth embodiment, for the detailed description, a case will be described in which the three-dimensional movement information calculation process according to the first embodiment is applied to the resiliency diagnosis.

FIG. 7 is a flowchart showing a sequence of the three-dimensional movement information calculation process according to the fourth embodiment.

First, time-series volume data group is collected from a superficial portion of a certain patient while the superficial portion is pressed by the two-dimensional array probe (Step S31). Next, the control unit 28 set a lattice-shaped or annular initial outline on the ROI or an entire region of volume data at a predetermined time phase on the basis of the instruction through the manipulation unit 24 (Step S32). The outline tracking section 31 obtains a position of each point (configuration point) forming the initial outline set for each volume data obtained at each time phase by performing a pattern matching process between two volume data (at different time phases) using a speckle pattern. Then, the outline tracking section 31 obtains coordinate information of the configuration point of the outline at each time phase by tracking process in time the configuration point of the initial outline (Step S33).

The area and volume calculating section 41 obtains the area of the outline on the basis of the coordinate information of each point forming the outline at each cardiac time phase (Step S34). In addition, as in the first embodiment, the area may be calculated by using, for example, the Heron's formula for calculating the area of the triangle on the basis of the length of three sides. The variation rate calculating section 43 calculates the variation rate from the area at the initial time phase on the basis of the calculated volume (Step S35).

The color determining section 45 determines a color corresponding to the degree of the area variation rate of the outline. The display control unit 20 displays the local area variation rate on the display unit 22 in a color display mode so as to be overlapped with a volume image, an MPR image, a Polar-Map image, and the like by using coordinate information of each position at each cardiac time phase and information displaying a color allocated to the position (Step S36).

According to the above-described configuration, in the resiliency diagnosis, the position coordinate information of each point three-dimensionally forming the tissue corresponding to the diagnosis target at each time phase, the area of the initial outline of the ROI or the like is obtained by using the position information, and then the variation rate is calculated on the basis of the result. Accordingly, as in the first, second, and third embodiments, since the quantitative value for evaluating the movement is calculated by using the three-dimensional position coordinate information without converting the wall movement information obtained by the three-dimensional tracking process into the two-dimensional information, it is possible to provide medical information with a higher degree of precision. Accordingly, for example, since the malignant tumor portion is harder than the normal portion, the area variation rate thereof is smaller than that of the normal portion, and hence it is possible to easily distinguish the normal portion from the malignant tumor portion.

In addition, the invention is not limited to the above-described embodiments, but the constituents thereof may be modified within the scope not departing from the spirit of the invention. As a detailed modified example, for example, the functions according to the above-described embodiments may be realized in such a manner that a program for executing the processes is installed in a computer such as a workstation and is loaded on a memory. At this time, a program capable of causing the computer to execute the method may be distributed while being stored in a storage medium such as a magnetic disk (a floppy (trademark) disk, a hard disk, and the like), an optical disk (a CD-ROM, a DVD, and the like), or a semiconductor memory.

Further, in the above-described embodiments, a case has been exemplified in which the process in accordance with the movement information calculation function is performed by using video data of the heart for at least one heartbeat obtained using the ultrasonic diagnostic apparatus. However, the technical spirit of the invention is not limited to this example. For example, the process in accordance with the movement information calculation function according to the above-described embodiments may be performed by using video data of the heart for at least one heartbeat obtained using a medical image diagnostic apparatus represented by an X-ray computed tomography apparatus and a magnetic resonance imaging apparatus, and the like other than the ultrasonic diagnostic apparatus. In addition, image data obtained by these medical image diagnostic apparatuses may be transmitted to a computer such as a PC or a workstation so as to be separated from the medical image diagnostic apparatuses.

Further, various inventions may be contrived by the appropriate combination of the plural constituents disclosed in the above-described embodiments. For example, several constituents may be omitted from all the constituents shown in the above-described embodiments. In addition, the constituents of the different embodiments may be appropriately combined.

What is claimed is:

1. An ultrasonic diagnostic apparatus comprising:
processing circuitry configured to:
obtain time-series volume data by ultrasonic scanning a three-dimensional region, including at least a part of a heart of a patient;
receive a setting of points, including at least three points, arranged for at least one of the time-series volume data;
track each of the points three-dimensionally among remaining time-series volume data, wherein the points define an outline of an endocardium surface or an epicardium surface;
calculate an area of a localized region on the endocardium surface or the epicardium surface for each of at least two time phases in a heartbeat, based on positions of the at least three of the tracked points; and
calculate a quantitative value, for evaluating movement of the localized region, based on the calculated area of the at least two time phases in the heartbeat.

2. The ultrasonic diagnostic apparatus according to claim 1,
wherein the processing circuitry calculates the area of the localized region of the part of the heart on the basis of the positions of each point, and calculates an area variation rate on the basis of the area.

3. The ultrasonic diagnostic apparatus according to claim 1,
wherein the processing circuitry further calculates a volume of the localized region of the part of the heart on the basis of the positions of each point, and calculates a volume variation rate on the basis of the volume.

4. The ultrasonic diagnostic apparatus according to claim 1,
wherein the time-series volume data is obtained by applying a pressure to the part of the heart or releasing the pressure applied thereto.

5. The ultrasonic diagnostic apparatus according to claim 1,
wherein the processing circuitry calculates the area of the localized region for evaluating the part of the heart by a unit based on an anatomical criterion.

6. The ultrasonic diagnostic apparatus according to claim 1, further comprising:
the processing circuitry creates a color image, having a color allocated thereto; and
a display which displays the color image.

7. The ultrasonic diagnostic apparatus according to claim 1, wherein the processing circuitry calculates three dimensional movement direction of each point through a pattern matching process.

8. The ultrasonic diagnostic apparatus according to claim 1,
wherein the processing circuitry calculates the quantitative value at each time phase using at least one of the area of the localized region of the endocardium surface or the epicardium surface.

9. The ultrasonic diagnostic apparatus according to claim 1, wherein the processing circuitry is configured to calculate areas of a plurality of localized regions on the endocardium surface or the epicardium surface for the each of at least two time phases.

10. An ultrasonic image processing apparatus comprising:
a memory which stores time-series volume data obtained by ultrasonic scanning a three-dimensional region, including at least a part of a heart, through an ultrasonic wave; and
processing circuitry configured to:
receive a setting of points, including at least three points, arranged for at least one of the time-series volume data,
track each of the points three-dimensionally among remaining time-series volume data, wherein the points define an outline of an endocardium surface or an epicardium surface;
calculate an area of a localized region on the endocardium surface or the epicardium surface for each of at least two time phases in a heartbeat, based on positions of the at least three of the tracked points; and
calculate a quantitative value, for evaluating movement of the localized region, based on the calculated area of the at least two time phases in the heartbeat.

11. The ultrasonic image processing apparatus according to claim 10,
wherein the processing circuitry calculates the area of the localized region of the part of the heart on the basis of the position of each point, and
wherein an area variation rate is calculated on the basis of the area.

12. The ultrasonic image processing apparatus according to claim 10,
wherein the processing circuitry further calculates a volume of the localized region of the part of the heart on the basis of the position of each point, and
wherein a volume variation rate is calculated on the basis of the volume.

13. The ultrasonic image processing apparatus according to claim 10,
wherein the time-series volume data is obtained by applying a pressure to the part of the heart or releasing the pressure applied thereto.

14. The ultrasonic image processing apparatus according to claim 10,
wherein the processing circuitry calculates the area of the localized region for evaluating the part of the heart by a unit based on an anatomical criterion.

15. The ultrasonic image processing apparatus according to claim 10, further comprising:
the processing circuitry creates a color image, having a color allocated thereto; and
a display which displays the color image.

16. An ultrasonic diagnostic apparatus comprising:
processing circuitry configured to:
obtain time-series volume data by ultrasonic scanning a three-dimensional region including at least a part of a heart of a patient;
receive a setting of points arranged for at least one of the time-series volume data;
track each of the points among remaining time-series volume data, wherein the points define an outline of an endocardium surface and an epicardium surface;
calculate volume of a localized region based on positions of tracked points of at least two time phases in a heartbeat, two facing surfaces of each of the localized region being local surfaces of the endocardium surface and the epicardium surface; and
calculate a quantitative value, for evaluating movement of the localized region, based on the calculated volume of the at least two time phases in the heartbeat.

17. An ultrasonic diagnostic apparatus comprising:
processing circuitry configured to:
obtain time-series volume data by ultrasonic scanning a three-dimensional region including at least a part of a heart;
receive a setting of points arranged for at least one of the time-series volume data;
track each of the points among remaining time-series volume data, wherein the points define an outline of a part of the heart;
calculate an area of a localized region on a curved surface of the heart based on positions of tracked points of at least two time phases in a heartbeat, the curved surface positioning between an endocardium surface and an epicardium surface of the heart; and
calculate a quantitative value, for evaluating movement of the localized region, based on the calculated area of the at least two time phases in the heartbeat.

18. An ultrasonic image processing apparatus comprising:
processing circuitry configured to:
a memory which stores time-series volume data for a three-dimensional region including at least a part of a heart;
receive a setting of points arranged for at least one of the time-series volume data;
track each of the points among remaining time-series volume data, wherein the points define an outline of an endocardium surface and an epicardium surface;
calculate volume of a localized region based on positions of tracked points of at least two time phases in a heartbeat, two facing surfaces of each of the localized region being local surfaces of the endocardium surface and the epicardium surface; and
calculate a quantitative value, for evaluating movement of the localized region, based on the calculated volume of the at least two time phases in the heartbeat.

19. An ultrasonic image processing apparatus comprising:
a memory which stores time-series volume data for a three-dimensional region including at least a part of a heart;
processing circuitry configured to:
receive a setting of points arranged for at least one of the time-series volume data,
track each of the points among remaining time-series volume data, wherein the points define an outline of a part of the heart;
calculate an area of a localized region on a curved surface of the heart based on positions of tracked points of at least two time phases in a heartbeat, the curved surface positioning between an endocardium surface and an epicardium surface of the heart; and
calculate a quantitative value, for evaluating movement of the localized region, based on the calculated area of the at least two time phases in the heartbeat.

* * * * *